United States Patent [19]

Ferguson

[11] Patent Number: 5,202,542
[45] Date of Patent: Apr. 13, 1993

[54] TEST SPECIMEN/JAW ASSEMBLY THAT EXHIBITS BOTH SELF-RESISTIVE AND SELF-INDUCTIVE HEATING IN RESPONSE TO AN ALTERNATING ELECTRICAL CURRENT FLOWING THERETHROUGH

[75] Inventor: Hugo S. Ferguson, Averill Park, N.Y.

[73] Assignee: Duffers Scientific, Inc., Poestenkill, N.Y.

[21] Appl. No.: 645,190

[22] Filed: Jan. 18, 1991

[51] Int. Cl.$^5$ .......................... G01N 3/18; H05B 3/00
[52] U.S. Cl. .................... 219/50; 219/10.47; 219/10.73; 219/10.57; 374/50; 374/51; 73/760; 73/766; 73/790
[58] Field of Search ................ 219/50, 10.47, 10.73, 219/10.57, 10.41; 374/45, 46, 49-52, 56, 57; 73/760, 766, 788-790, 813, 818, 821, 822

[56] References Cited

U.S. PATENT DOCUMENTS

| | | | |
|---|---|---|---|
| 2,426,985 | 9/1947 | Darmara | 219/10.43 |
| 3,100,253 | 8/1963 | O'Connor | 219/20 |
| 3,772,492 | 11/1973 | Brogden et al. | 219/10.79 |
| 4,627,259 | 12/1986 | Andersson et al. | 219/10.43 |
| 4,788,396 | 11/1988 | Maugein et al. | 219/10.43 |
| 5,055,648 | 10/1991 | Iceland et al. | 219/10.47 |

FOREIGN PATENT DOCUMENTS

| | | | |
|---|---|---|---|
| 585825 | 10/1933 | Fed. Rep. of Germany | 374/46 |
| 1237322 | 6/1960 | France | 374/46 |
| 3-111517 | 5/1991 | Japan | 219/10.57 |
| 675632 | 6/1976 | U.S.S.R. | |
| 974208 | 11/1982 | U.S.S.R. | 374/51 |

OTHER PUBLICATIONS

Hiroo Suzuki, "Heater For Metal Sample", Patent Abstracts of Japan, vol. 4, No. 51 (Apr. 17, 1980).
Derwent Publications, Ltd., "As UKR Strength Problems", *Soviet Inventions Illustrated*, Section EI, Week 8932 (Sep. 20, 1989).

Primary Examiner—Bruce A. Reynolds
Assistant Examiner—John A. Jeffery
Attorney, Agent, or Firm—Peter L. Michaelson

[57] ABSTRACT

Apparatus either for a specimen that is to be held in a jaw assembly of, for example, a dynamic thermal-mechanical testing system or for the jaw assembly itself wherein the specimen or jaw assembly, respectively, exhibits both self-resistive and self-inductive heating whenever a sufficiently large alternating (AC) electrical current is passed serially therethrough. In one embodiment, the specimen (200, 300) is fabricated from a material which undergoes self-resistive heating and in which suitable levels of eddy currents can be induced by and also includes an appropriately shaped heating section (205, 206; 305, 306) situated near each of two opposing ends thereof. In another embodiment, a metallic conductor (403, 403'; 503) is fabricated from a material which undergoes self-resistive heating, in which suitable levels of induced eddy currents can occur and which contains appropriately shaped and sized heating sections (406, 407; 406', 407'; 512, 512'). Such a conductor is situated in each jaw assembly (401, 401'; 500). Each conductor abuts against and is in electrical contact with an opposing end-face of a specimen. Whenever current is passed through either embodiment, these heating sections (205, 206; 305, 306; 406, 407; 406', 407'; 512, 512') will exhibit both self-resistive and self-inductive heating wherein the amount of additional heat generated through self-induction and propagating into the ends of the specimen can be set to compensate for heat loss that would otherwise occur from the ends of the specimen into the neighboring jaw assembly thereby assuring that substantially no longitudinal temperature gradients are established either along the mid-span region of the specimen or along the entire specimen while heating current passes therethrough. The size and shape of each such heating section governs the amount of additional heat that will be generated therein.

35 Claims, 5 Drawing Sheets

TEST SPECIMEN/JAW ASSEMBLY THAT EXHIBITS BOTH SELF-RESISTIVE AND SELF-INDUCTIVE HEATING IN RESPONSE TO AN ALTERNATING ELECTRICAL CURRENT FLOWING THERETHROUGH

BACKGROUND OF THE DISCLOSURE

1. Field of the Invention

The invention relates to apparatus either for a specimen that is to held in a jaw assembly of, for example, a dynamic thermal-mechanical testing system or for the jaw assembly itself wherein the specimen or jaw assembly, respectively, exhibits both self-resistive and self-inductive heating whenever a sufficiently large alternating electrical current is passed serially therethrough.

2. Description of the Prior Art

Metallic materials play an indispensable role as an essential component of an enormous number of different products. One crucial property of such materials is their ability to conduct electricity. Absent operation at superconductive temperatures, a metallic object possesses a resistance to electrical current flow based upon its cross-sectional size, length and resistivity. Owing to this resistance, the object will generate heat whenever an electric current is passed therethrough. This form of heating is the so-called "self-resistive heating". Self-resistive heating finds use in a wide number of diverse applications.

Different materials, including those that are metallic, possess widely varying mechanical, metallurgical and other properties. As such, the specific properties required of a material for use in a given application are first determined followed by selection of a specific material that exhibits appropriate minimum values of these properties. An essential step in selecting a specific material is first to determine its properties of interest by testing specimens of each such material being considered.

Materials are tested in a wide variety of different ways. One such way, which is experiencing substantially increasing use, is dynamic thermal-mechanical testing. Here, a specimen is gripped at each of its two ends in a jaw system. The specimen is typically in the form of a small cylinder or sheet section of a given material and has a substantially uniform circular, rectangular or square cross-sectional area. An electric current is serially passed from one jaw assembly to another and through the specimen to generate a rapid, but controlled, heating rate throughout the specimen. Simultaneously therewith, various measurements are made of the specimen. Depending upon the specific measurements being made, the specimen either may or may not undergo controlled deformation while it is being heated. If the specimen is to be deformed, then this deformation can be accomplished by moving one of the two jaw assemblies, at a controlled rate with respect to the other, in order to impart either a controlled tensile or compressive force to the specimen. Alternatively, the specimen can be controllably struck by one of the jaw assemblies in order to impart a forging force thereto while current is passing through to the specimen to controllably heat it. Physical measurements, such as illustratively specimen dilation and temperature, are typically made while heating and deformation are simultaneously occurring. This testing not only reveals various static properties of the specimen material itself, such as its continuous heating transformation curve, but also various dynamic properties, such as illustratively hot stress vs. strain rates and hot ductility; the dynamic properties being particularly useful in quantifying the behaviour of the material that will likely occur during rolling, forging, extrusion or other material forming and/or joining operations. One system that provides excellent dynamic thermal-mechanical testing is the GLEEBLE 1500 system manufactured by the Duffers Scientific, Inc. of Poestenkill, N.Y. (which also owns the registered trademark "GLEEBLE" and is the present assignee). This system advantageously heats the specimen self-resistively in order to generate transverse isothermal planes throughout the entire specimen. Specifically, since each specimen generally has a substantially uniform transverse cross-section throughout its length, then the current density will be uniform throughout the entire specimen which will cause uniform heating over the entire cross-section.

The specimens used in dynamic thermal-mechanical testing usually fall within a fairly wide range of sizes. Tensile specimens are often cylindrical in shape and may be on the order of approximately 6 to 12 millimeters in diameter and approximately 10 to 20 centimeters in length. Tensile specimens having a rectangular cross-section are also used from time to time. Compression specimens also tend to be cylindrical in shape and may be on the order of 8 approximately to 15 millimeters in diameter and also approximately 10 to 20 millimeters in length. For simulating strip annealing, a suitable specimen will have a rectangular cross-section and may be on the order of approximately 1 millimeter thick and approximately 170 millimeters wide and approximately 300 millimeters long.

Regardless of the specific specimen that is to undergo dynamic thermal-mechanical testing, relatively high currents generally must be passed through the specimen in order to produce the requisite level of self-resistive heating therein. The amount of electrical current that is required to heat a specimen to a given temperature and/or at a given heating rate generally depends upon a number of factors, for example: the specific heat of the material; its resistivity; the geometric shape of the specimen, such as its cross-sectional area and length; heat loss from the specimen to its surroundings, principally including but not limited to the jaw system used to grip the specimen; and the value of the final temperature to be attained. In practice and owing to the low resistances of most specimens, generally only a few volts or less need to be applied across the specimen to conduct the required current therethrough.

As noted above, a specimen is securely held within a dynamic thermal-mechanical testing system between two jaw assemblies and specifically by a grip contained within each such assembly. A series path is established to route heating current from one jaw assembly through the specimen to the other jaw assembly. For several reasons, the grips and jaw assemblies must be substantially larger in size than the specimen itself. First, electrical connections must be made to opposite ends of the specimen to conduct the current required to heat the specimen but without causing an appreciable voltage drop across each jaw assembly. As such, the jaw assemblies must be sufficiently large to provide a very low resistance path for the high levels of current. Second, to prevent the jaw assemblies, particularly if they are not water-cooled, from adversely melting or softening during high temperature testing, the jaw assemblies must provide a sufficient mass so that for a given current level, the jaw assemblies will remain appreciably cooler than the specimen and will heat at a significantly lower rate. Third, mechanical loads, as noted above in the form of tensile, compressive or forging forces, are applied through the jaw assemblies to deform the specimen while it is heating. As such, the jaw assemblies must be of sufficient size to safely transmit these forces to the specimen without experiencing any deformation themselves.

A number of dynamic thermal-mechanical tests require that essentially no longitudinal thermal gradients exist along the mid-span of the specimen. However, in practice, thermal gradients often occur between the ends of the mid-span during heating. The reason for this stems from the fact that the jaw assemblies, being of considerably greater thermal mass than the specimen, tend to conduct considerable quantities of heat away from the ends of the specimen while that specimen is being self-resistively heated. This, in turn, causes the opposing ends of the specimen to be significantly cooler than its mid-span.

Either one of two well-known techniques is often used to remedy this heat loss; however, each of these techniques possesses one or more drawbacks which disadvantageously limits its utility. First, both jaw assemblies themselves can be heated to the specimen temperature to prevent heat from being conducted from the specimen to these assemblies. Not only does this technique require the addition of supplementary heating equipment to heat the jaw assemblies but also necessitates, along with the added cost of this equipment, that a substantial amount of energy be consumed to heat these assemblies. In addition, if the jaw assemblies are heated to a sufficiently high temperature, these assemblies may become too ductile and will themselves deform while mechanical forces are being applied therethrough to the specimen. Second, for a given current passing through the specimen, the temperature of each end of that specimen can be increased by appropriately reducing the cross-sectional area of the specimen material appearing at that end. While, this technique is very reproducible, it adversely limits the maximum rate at which the entire specimen can be heated. Specifically, this technique involves drilling a number of holes into each end of the specimen near its jaw contact area in order to reduce the amount of material present thereat. Inasmuch as the material is reduced at each end, the cross-sectional area of the specimen at that end is decreased which, in turn, locally increases the current density occurring thereat. For a given amount of current passing through the specimen, the increased current density in the ends locally increases the heating rate and the final temperature of each end. Unfortunately, to generate sufficient heat at the ends to adequately compensate for the heat being lost from the specimen to the grips, a sufficient amount of material must be removed from each end of the specimen which may adversely cause the heating rate thereat to rise too rapidly to the point where specimen material melts and burns off each end prior to the mid-span of the specimen attaining a desired final temperature. To prevent this effect, the self-resistive heating current must be appropriately reduced which, in turn, adversely reduces the rate at which the entire specimen can heat. For example, an adequate cross-sectional reduction may necessitate that the cross-sectional area of each end be reduced to approximately $\frac{1}{4}$ of its original value. However, to avoid excessive end temperatures from occurring in the specimen, the current that will pass through the specimen will need to be appropriately reduced such that the maximum heating rate of the entire specimen is only $\frac{1}{4}$ of the value that would otherwise be used if the specimen had a uniform cross-sectional area throughout. Unfortunately, limiting the heating rate in this fashion artificially limits the thermal behaviour of the specimen that can be measured by the testing system. Furthermore, this technique also tends to decrease the mechanical strength of the specimen to the point where purely mechanical testing thereof (e.g. application of tensile, compressive or forging forces) may not be possible. Specifically, as material is removed from each end of the specimen, the mechanical strength of that end decreases below that of the mid-span which, during the application of an appropriate force is likely to cause the specimen to prematurely fail at its end(s).

Thus, a need exists in the art for a technique for use in conjunction with, for example, a dynamic thermal-mechanical testing system that can compensate for conductive heat loss occurring from a specimen under test to the jaw assemblies without requiring the use of heated jaw assemblies and which does not appreciably limit the maximum rate at which the entire specimen can be heated or reduce the strength of a specimen to be used for purely mechanical room testing.

SUMMARY OF THE INVENTION

My invention overcomes the deficiencies associated with techniques known in the art for remedying the conductive heat loss that occurs from the specimen ends to the jaw assemblies in, for example, a dynamic thermal-mechanical testing system. Through use of my invention, a specimen can be secured between grips in two opposing jaw assemblies and heated by an alternating (AC) electrical heating current passing serially through the jaw assemblies and the specimen but without establishing substantially any longitudinal thermal gradients either throughout the entire specimen or throughout its mid-span region. My inventive technique advantageously does not require the use of separately heated jaw assemblies and does not artificially limit the rate at which the entire specimen can be heated or reduce the strength of a specimen used for purely mechanical testing.

Specifically, my invention involves appropriately shaping either both opposing ends of the specimen itself or metallic conductors that are placed in abutting electrical contact with the specimen ends and situated in the jaw assemblies such that the specimen ends are heated both self-resistively and self-inductively by the alternating (AC) heating current, at power line frequencies, that passes through the specimen and, when used, the conductors.

In one embodiment, the specimen is fabricated from a material in which a suitable amount of eddy currents can be induced and that is shaped, such as by appropriately bending the specimen, to possess illustratively two (or more) heating sections each situated near an opposing end of the specimen. Each such section is formed to illustratively have two adjacent, though non-abutting, serially connected legs. The legs in each section form illustratively a "hat" or inverted "U" shape, though triangular and other shapes could also be used. Within each section, the current that flows through each leg induces eddy current flow in the other leg which inductively heats the latter. Inasmuch as current flows in an opposite direction in each leg in a section with respect to the other leg therein, both legs in that section self-inductively heat. The resulting self-inductive heat, as well as the self-resistive heat, produced in both legs adds to the self-resistive heat generated in the specimen by the current flowing therethrough. The amount of heat that is inductively generated is governed by the size and shape of each section, including the length of each leg as well as the distance between the legs. By choosing the appropriate size and shape of each section, the amount of additional heat generated through self-induction can advantageously compensate for any heat that is conducted from the specimen ends into both jaw assemblies. This, in turn, permits a uniform temperature, without substantially any longitudinal temperature gradients, to be established end-to-end throughout the midspan of the specimen by an alternating current passing therethrough. Alternatively, a metallic conductor, capable of generating self-resistive heat and having a suitably amount of eddy currents induced therein, with one or more appropriately shaped and sized heating sections, can be incorporated into each jaw assembly itself. An end of each of these conductors abuts against and is in electrical contact with an opposing end-face of a specimen to provide good thermal and good electrical contact therebetween. This alternative arrangement advantageously permits a desired longitudinal thermal gradient to be established end-to-end along the entire specimen.

By incorporating heating sections within a specimen, my inventive specimen provides the feature of permitting grips situated in the jaw assemblies to remain at or near room temperature in order to exploit the room temperature mechanical properties, such as high room temperature strength or high low temperature hardness, of the grip material, while, through self-inductive and self-resistive heating of the specimen ends, permitting the mid-span region of the specimen (the portion of the specimen situated between the heating sections) to be uniformly and electrically heated to a significantly higher temperature without substantially any longitudinal temperature gradients appearing therein.

In addition, by incorporating appropriate heating sections within the jaw assemblies themselves rather than in a specimen, my invention provides the feature of very easily introducing supplemental heat into each jaw assembly. While energy is consumed in heating these sections, the amount of this energy, while significant, is advantageously considerably smaller than that which would ordinarily be consumed if the jaw assemblies and/or specimen ends were to be heated using an additional source of energy.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the broad teachings of my invention can be readily utilized in conjunction with nearly any self-resistively heated material, in which a suitable amount of eddy current can be induced therein, in order to increase the amount of heat generated in that material beyond that obtainable through only self-resistive heating. In essence, a material formed in accordance with my invention generates both self-resistive and self-inductive heat from a single common source of alternating (AC) heating current passing through the specimen. Nevertheless, for purposes of illustration and to simplify the following discussion, I will specifically describe my invention in the context of use with specimens of typical conductive materials that can be tested with a dynamic thermal-mechanical materials testing system, such as illustratively the GLEEBLE 1500 system manufactured by the Duffers Scientific, Inc. of Poestenkill, N.Y. (which also owns the registered trademark "GLEEBLE" and is the present assignee) and with various jaw assemblies that can be used in such a system.

Figure 1:
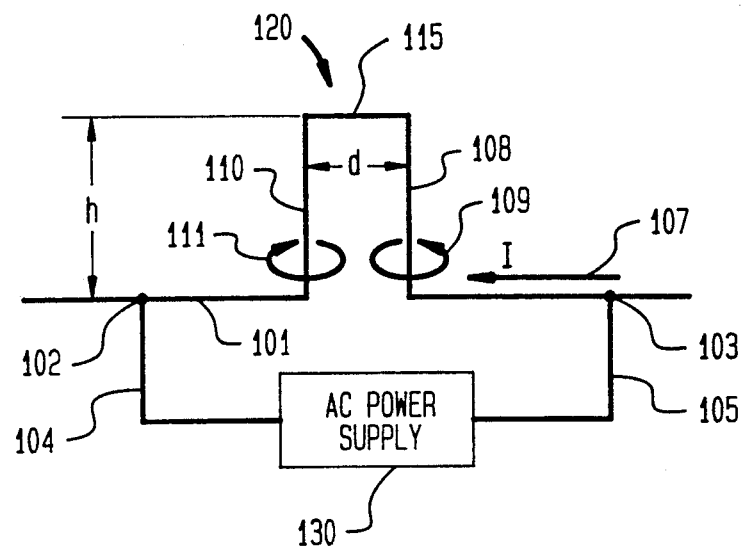
FIG. 1 shows a simplified schematic diagram of a piece of material, illustratively a wire, appropriately formed which undergoes both self-resistive and self-inductive heating by virtue of a single alternating (AC) current (I) flowing therethrough.

To facilitate reader understanding, FIG. 1 shows a simplified schematic diagram of a piece of material which is formed in conjunction with my inventive teachings and that undergoes both self-resistive and self-inductive heating by virtue of a alternating (AC) current (I) flowing therethrough. Here, the conductive material, illustratively wire 101, has a uniform transverse cross-sectional area and a constant electrical resistance per unit length. Furthermore, the material is one in which a suitable amount of eddy currents can be induced by an external magnetic field. Wire 101 is serially connected at points 102 and 103 and via respective leads 104 and 105 to power supply 106. This supply provides a source of low voltage high current AC power at power line (e.g. 50 or 60 Hz) frequencies. For one half-cycle of applied power, current (I) flows through material 101 in the direction shown by arrow 107; during the next half-cycle, the direction of current flow is reversed from that shown. Owing to the uniform resistance/unit length of wire 101, current (I) will establish a constant self-resistive heating rate along the entire length of the wire. As such, each incremental length of the wire will generate the same amount of self-resistive heat.

As shown, wire 101 is fabricated to contain heating section 120 formed of opposing legs (illustratively shown as vertical risers) 108 and 110, having a height h and a separation d, connected by transverse leg 115 of length d. The three legs in this section form illustratively a "hat" or inverted "U" shape. With this arrangement, current flowing in the direction indicated by arrow 107 generates circular lines of magnetic flux in the directions indicated by arrows 109 and 111 around legs 108 and 110, respectively. Similar lines of flux, though reversed in direction, are generated by current (I) as it flows in the direction opposite to that shown by arrow 107. The magnetic flux lines generated by leg 108 penetrate leg 110 and cause eddy currents to flow therein. Similarly, the magnetic flux lines generated by leg 110 penetrate leg 108 and cause eddy currents to flow therein. These eddy currents, formed by inductive coupling between the two legs, also generate heat, hereinafter referred to as "self-inductive heat", due to the resistance of the material in each leg through which these eddy currents flow. The magnitude of the eddy currents depends upon the strength of the magnetic field generated by each leg in section 120 and the amount of that field which penetrates into the other leg situated in that section. Either reducing the inter-leg spacing d between the vertical risers or increasing the length h of each such riser will increase the magnetic coupling between the risers, the eddy currents induced therein and hence the amount of self-inductive heat generated thereby.

Through this arrangement, the total amount of heat generated in wire 101 is the sum of the self-resistive heat and the self-inductive heat. Inasmuch as both sources of heat are generated by the same current (I), this arrangement permits more heat to be generated in the wire than that which would result from self-resistive heating alone, i.e. the heat that would result in the wire if section 120 were to be replaced by a straight length of wire.

Figure 2:
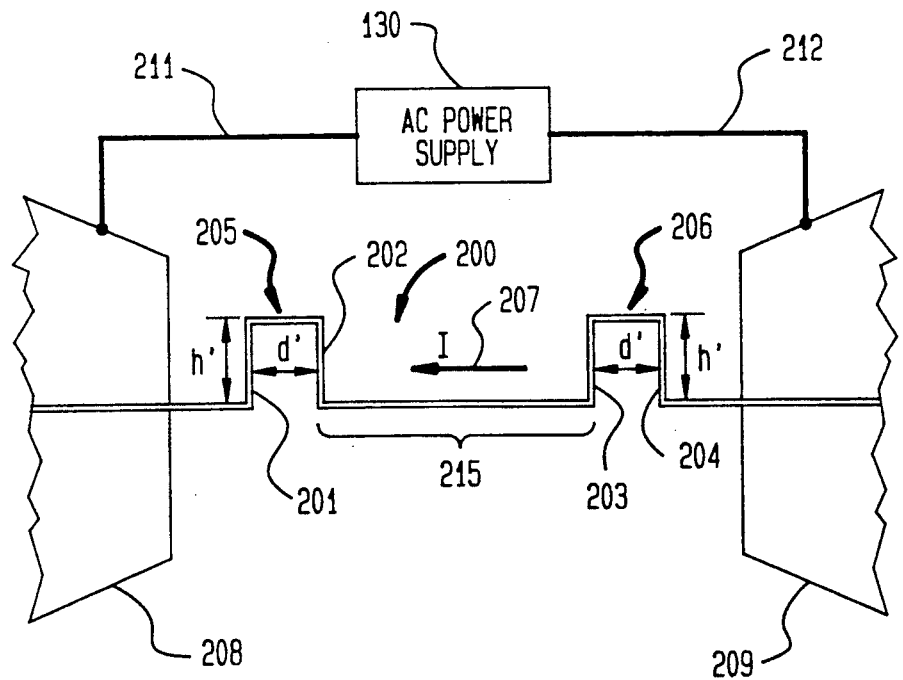
FIG. 2 shows a simplified diagram of an embodiment of a test specimen formed in accordance with my inventive teachings which is held between two jaw assemblies of a dynamic thermal-mechanical testing system and that experiences both self-resistive and self-inductive heating.

With the above in mind, FIG. 2 shows a simplified diagram of an embodiment of test specimen 200 formed in accordance with my inventive teachings which is held between two jaw assemblies 208, 209 of a dynamic thermal-mechanical testing system and that experiences both self-resistive and self-inductive heating. Here, specimen 200, shown in longitudinal cross-section, is illustratively a strip annealing test specimen through which alternating current (I) at power line frequencies will be passed according to a pre-determined test schedule to heat treat the specimen in a manner that simulates a desired strip annealing production process. Specimen 200, which has a transverse rectangular cross-section, contains two heating sections 205, 206 separated by mid-span region 215. The mid-span region typically has a length of approximately 200 millimeters. The entire specimen has a uniform width typically on the order of 150 millimeters and a uniform thickness ranging between approximately 0.25 to 1.5 millimeters depending upon the specific annealing process being simulated.

As shown, power supply 130 is connected through leads 211 and 212 to jaw assemblies 208 and 209. These assemblies, which are highly conductive, collectively grip specimen 200 at opposing contact regions thereon and provide electrical connections for longitudinal current flow through the specimen. During one half-cycle of applied AC power, current flows through the specimen in the direction shown by arrow 207, and reverses its flow during the next half-cycle thereof. Heating sections 205 and 206 are formed of two opposing legs (also illustratively shown as vertical risers) 201, 202 and 203, 204, connected by transverse legs 205 and 206, respectively. The opposing legs in each section have the same height h' and are separated by the same spacing d'. Each of these sections generates heat in the same manner as discussed above. As such, the current flow through specimen 200 induces eddy current flow within sections 205 and 206 and provides self-inductive heat in legs 201, 202, 203 and 204 which, in turn, raises the temperature of these legs in excess of that which would occur therein through self-resistive heating alone in each of these legs. Consequently, if the jaws assemblies and the mid-span region are at lower temperatures than these legs, then a portion of the heat generated in these legs flows through specimen 200 to jaw assemblies 208 and 209 and another portion flows into mid-span region 215.

By properly sizing and shaping each of the heating sections 205 and 206, both the self-inductive and self-resistive heat generated therein can substantially, if not totally, compensate for the entire self-resistive heat loss that occurs from the specimen into the jaw assemblies and thereby permit a substantially uniform heating rate to occur entirely throughout mid-span region 215 without substantially any longitudinal temperature gradients appearing therein. By increasing or decreasing the spacing d' between or the height h' of each vertical riser, the amount of self-inductive heat that can be generated in each section, for a given current flow, can be correspondingly changed. For example, increasing the height h' or decreasing the spacing d' will increase the self-inductive heat. Illustratively, for a steel specimen having a thickness of 1 millimeter, the height h' of vertical risers 201, 202, 203 and 204 can each be 12 millimeters with the spacing d' between two adjacent risers also being 12 millimeters. Ideally, to prevent excessive temperatures from appearing in the specimen material situated near the ends of mid-span region 215 and establishing essentially no longitudinal temperature gradients in the mid-span region, the size and shape of the legs in each heating section should be set such that the self-inductive and self-resistive heat generated thereby matches the heat losses occurring from the specimen to jaw assemblies 208 and 209. Once the legs are so set, then during subsequent heating, the temperature of the heating sections will substantially, if not precisely, equal and track the temperature occurring at the middle of specimen 200 thereby producing essentially no thermal gradients occurring along mid-span region 215 in the specimen. Alternatively, if desired, the size and shape of each heating section can be suitably adjusted to permit a longitudinal thermal gradient to appear in the mid-span region which increases towards the center of the mid-span region or decreases therefrom. Moreover, in order to establish a desired longitudinal temperature gradient throughout the mid-span region, a testing specimen, fabricated in accordance with my inventive teachings, can even contain heating sections that have unequal sizes and/or different shapes. Inasmuch as each heating section is mechanically established thereby subject to excellent dimensional control and the heating current flowing through the specimen can be readily controlled quite precisely, nearly any desired thermal gradient can not only be easily and accurately generated throughout the entire mid-span region of the testing specimen but is also accurately reproducible.

To assure that sufficient heating occurs within sections 205 and 206, specimen 200 must possess the ability to generate self-resistance heat and have a sufficient amount of eddy currents induced therein. Specifically, eddy currents, which inductively heat a material, result from changing magnetic flux lines that penetrate into that material. Various factors govern the amount of inductive heating that can occur; namely, inter alia, the magnetic properties of the material itself, such as its magnetic permeability as well as its magnetic path length and shape; the field strength available to induce eddy current flow in the material; and the electrical resistance of the material (to usually circular eddy current flow therein). Materials of higher resistance will generate more inductive heat from a given level of eddy current flow than materials having lower resistance; however, larger eddy current flow can be established in such lower resistance materials for a given field strength. The magnetic permeability of ferromagnetic materials is relatively high, such as several thousand, which, in turn, permits these materials to exhibit increased self-inductive heating over paramagnetic or diamagnetic materials, i.e. materials that have a magnetic permeability slightly larger than or less than one. However, as a ferromagnetic material is heated above its so-called and well-known "Curie temperature", i.e. the temperature at which that material becomes paramagnetic and its permeability decreases to slightly above one, its induced field strength decreases as does the self-inductive heating generated therein. I have experimentally found that although the resulting self-inductive heat that is generated by a ferromagnetic material is less whenever that material is heated above its Curie temperature than that which results whenever that material remains below this temperature, the resulting decrease is modest. This indicates that the effect of the shape and size of each heating section, particularly on the magnetic coupling therein and the eddy currents flowing thereby, is more predominant than the amount of heat generated in each section through ferromagnetic effects.

Figure 4:
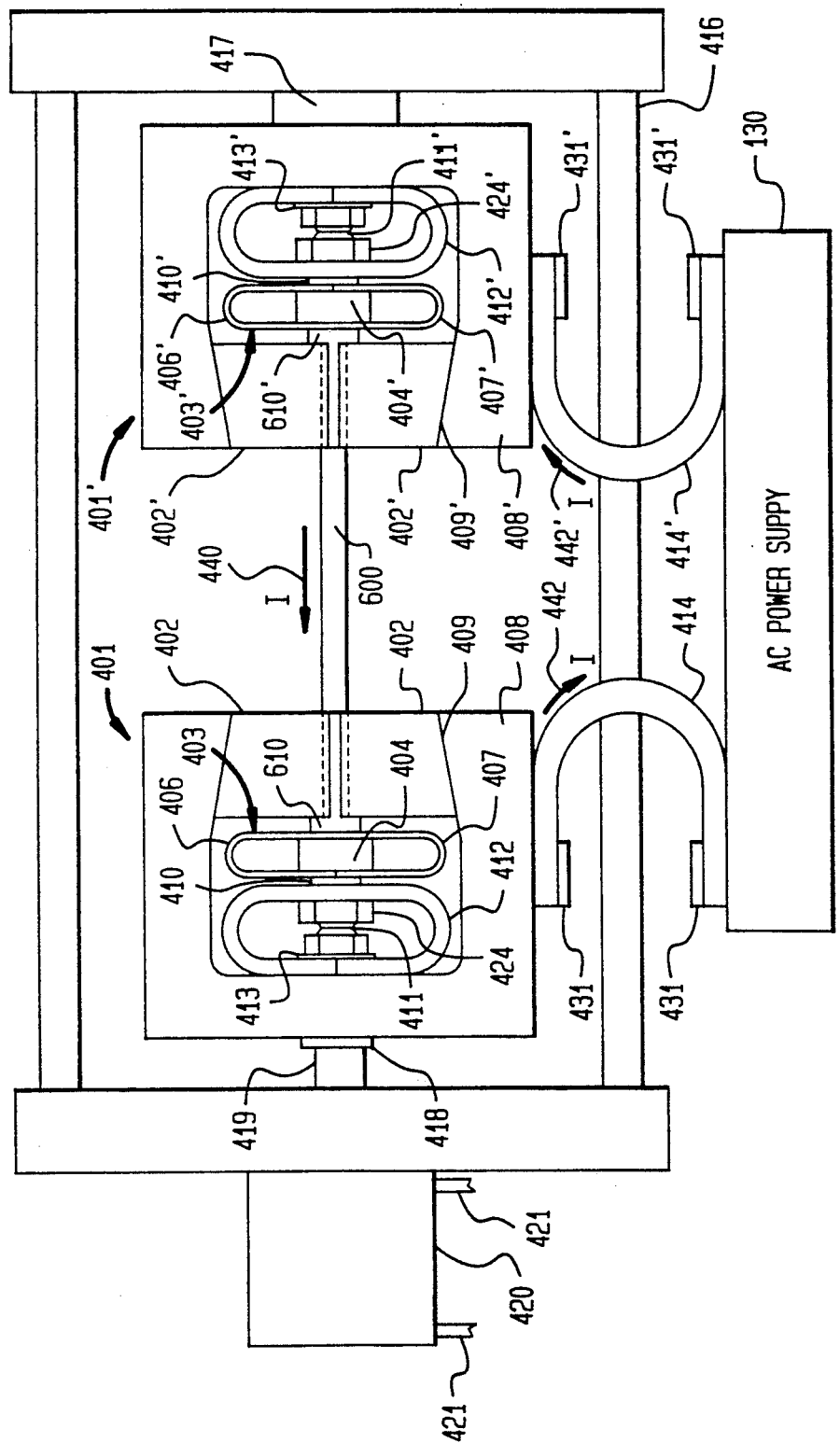
FIG. 4 shows a detailed plan view of a tension/compression test apparatus which forms a portion of the dynamic thermal-mechanical testing system and that incorporates jaw assemblies fabricated in accordance with my inventive teachings.

Furthermore, as the frequency (particularly the rate of change) of the external magnetic field increases, the amount of self-inductive heat that will be generated in the material also increases. However, as a result of well-known "skin effects", these eddy currents will penetrate less deeply into the material as the frequency of the field increases. As such, typical induction heating applications rely on using heating currents with frequencies up to approximately 500 kHz. At power line frequencies, the external magnetic field will fully penetrate the material, even a relatively thick cross-section thereof, though the amount of inductive heat that will be generated thereby is relatively small as contrasted to that which will occur at higher frequencies. Nevertheless, I have experimentally found that the amount of self-inductively and self-resistively generated heat produced in even relatively small sized heating sections, such as sections 205 and 206, when power line frequency heating currents are used is more than adequate to compensate for heat loss that occurs to the jaw assemblies, such as assemblies 208 and 209. Since the affect of ferromagnetism does not markedly change the amount of self-inductive heat that is generated at typical test temperatures, specimen 200 (as well as conductors 403 and 403' shown in FIG. 4, 503 shown in FIG. 5, and 803 and 803' shown in FIG. 8—all of which are discussed in detail below), specimen 200 can be readily fabricated from suitable ferrous or non-ferrous materials.

Jaw assemblies 208 and 209 may be water cooled to maintain a relatively low jaw temperature or allowed to increase in temperature; the latter merely relying on non-forced air cooling. Inasmuch as the heat loss that occurs to water cooled jaw assemblies will be substantially higher than that which occurs to non-forced air cooled jaw assemblies, the shape and size of heating sections 205 and 206 will need to be adjusted to generate more self-inductive heat for specimens being gripped by water cooled jaw assemblies than for non-forced air cooled jaw assemblies in order to properly offset the heat loss that occurs to the water cooled jaw assemblies.

Figure 3:
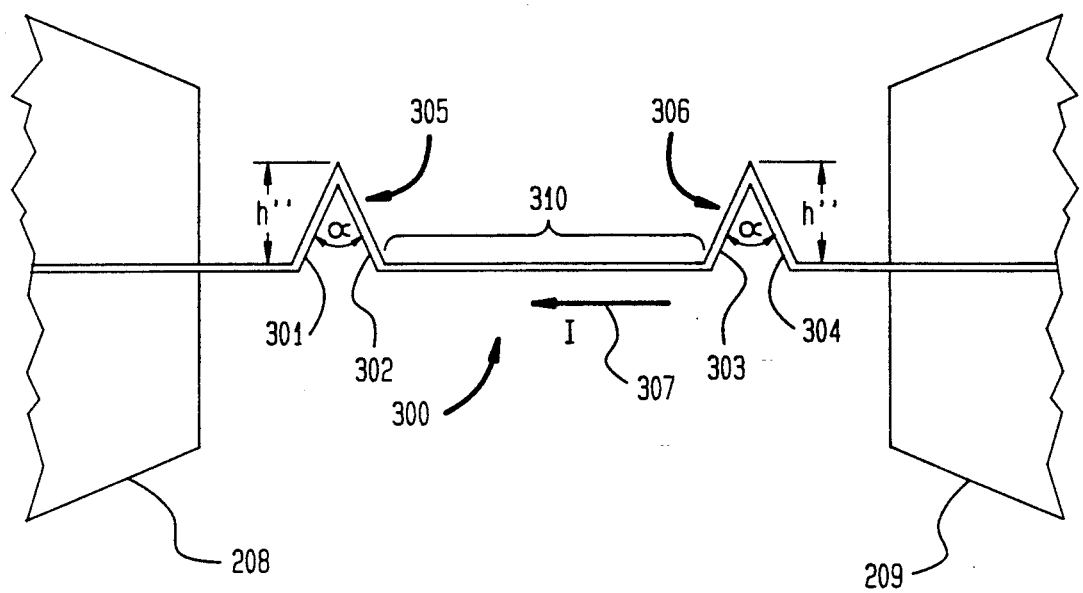
FIG. 3 shows a simplified diagram of an alternate embodiment of a test specimen formed in accordance with my inventive teachings which is also held between two jaw assemblies of a dynamic thermal-mechanical testing system and that also experiences both self-resistive and self-inductive heating.

Clearly, the specimen can be fabricated to use other non-rectangular shapes for each heating section. Inasmuch as the amount of self-inductive heat required in most sheet metal specimens tends to be relatively small, a variety of non-rectangular shaped heating sections can be used. In this regard, FIG. 3 shows a simplified diagram of an alternate embodiment of a test specimen, here having triangularly-shaped heating sections, formed in accordance with my inventive teachings which is also held between two jaw assemblies of a dynamic thermal-mechanical testing system and that also experiences both self-resistive and self-inductive heating. As shown, jaw assemblies 208 and 209 grip test specimen 300 which contains triangularly-shaped heating sections 305 and 306 separated by mid-span region 310. Here, sections 305 and 306 are formed by intersecting legs 301, 302 and 303, 304, respectively, which subtend a pre-defined angle, $\alpha$, therebetween. As this angle is increased or both legs in a section are shortened, the amount of magnetic induction and self-inductive heating that is produced in each such leg will correspondingly decrease. Correlatively, smaller angles or lengthened legs will tend to increase the amount of magnetic induction and self-inductive heating produced in each section. As an example, if specimen 300 has a thickness of 1 millimeter, then legs 301, 302, 303 and 304 that form sections 305 and 306 may each be approximately 11 millimeters in length with the height, $h''$, of each section being approximately 5 millimeters. As a consequence of these dimensions, each section will heat more rapidly than mid-span region 310 with excess heat flowing from that section both into the mid-span region and into the nearby jaw assembly. Illustratively, if sufficient current is applied to specimen 300 to generate a heating rate of 20° Centigrade/second (C/sec) in mid-span region 310, then sections 305 and 306 will heat somewhat faster than the mid-span region. If sufficient current is used to generate a heating rate of 40° C./sec in the mid-span region, then the temperature of the mid-span region will considerably lag that of both heating sections. Specifically, after passing current through specimen 300, with the sizes set forth above, to heat the center of the mid-span region at a rate of 40° C./sec to a temperature of 800° C., both heating sections 305 and 306 may be approximately 100° C. warmer than the center of mid-span region 310. The size and shape of sections 305 and 306 would normally be set to minimize over temperature at the specimen ends for the chosen heating rate and to account for specimen cross-section, type of material, maximum temperature and specimen mid-span length in order to provide essentially no longitudinal temperature gradient throughout the mid-span of the specimen.

Forming such a triangular shape for each heating section advantageously requires one less bend than forming a rectangular "hat" shape in each such section and is thereby easier to fabricate than the "hat" shape. During one half-cycle of AC current, heating current flows through specimen 300 in the direction shown by arrow 307, while the direction reverses during the next successive half-cycle. To simplify the figure, power supply 130 and its associated leads have been purposely omitted therefrom.

To experimentally demonstrate the performance of a heating section in either ferrous or non-ferrous materials for use in illustratively a GLEEBLE 1500 testing system, I prepared 50 millimeter wide specimens from 1.5 millimeter thick sheet stock. Separate specimens were fabricated from carbon steel and from type 304 stainless steel and type 6061 T6 aluminum, the latter two exhibit no allotropic transformations and no ferromagnetism. One triangular heating section, such as e.g. section 305 shown in FIG. 3, was formed in each specimen near an end thereof and within 35 millimeters inward of the jaw contact area therefor. For each carbon steel specimen, the section was 12 millimeters on each side and 12 millimeters wide at its base; while a similarly shaped heating section 25 millimeters on each side and 6 millimeters wide at its base was formed in each stainless steel and aluminum specimen. The thermal performance of each specimen was tested through the GLEEBLE 1500 system using a heating schedule during which that specimen was heated at a fixed heating rate of either 5° C./second or 50° C./second to 400° C., then held at that temperature for approximately 90 seconds, then heated at the same rate to 800° C. and then held thereat again for approximately 90 seconds followed by cooling. Pneumatically operated wedge grips were used to assure a substantially uniform gripping force along the entire width of the specimen. During testing, the jaw assemblies were also water-cooled to remain at room temperature. Separate thermocouples were spot welded to each specimen 35 millimeters inward of each jaw contact area—one of which was situated slightly inward of the heating section—and also at the center of the mid-span region. The output of each thermocouple was periodically sampled by the GLEEBLE 1500 system throughout a test interval defined by the heating schedule. Inasmuch as carbon steel has a higher conductivity than stainless steel, one would expect that it would tend to be somewhat more difficult to appropriately size the heating sections in order to maintain relatively small thermal gradients over a relatively long specimen. The measured test data confirmed this. Furthermore, since stainless steel has a relatively high resistance, the air flow around such specimens needs to be restricted in order to prevent surface cooling. As such, each stainless steel specimen was covered with a ceramic blanket during testing. Vacuum testing could alternately be used and would generate the same test results. Based upon the measured data, the temperatures of the stainless steel and aluminum specimens at both the heating section and the mid-span region tracked each other with no appreciable differences occurring therebetween during the entire test interval for heating at either 5° or 50° C./second. As expected and due to conductive heat losses that occurred from one end of the specimen to a jaw assembly, the temperature of the specimen end located opposite to that situated near the heating section tended to remain significantly cooler than that measured at the other two locations thereon. Similar results occurred in the carbon steel specimens though with a somewhat increased variation occurring between the temperatures at the center of the mid-span region and the heating section during the holding and cooling intervals. For specimens heated at 5° C./second, the maximum variation amounted to approximately 50° C.; while for specimens heated at 50° C./second, the maximum variation amounted to approximately 30° C. It is expected that these small variations could be removed by appropriately modifying the size of the heating sections in the carbon steel specimens. No appreciable variations occurred in the carbon steel specimens during heating.

Testing specimens similar in shape to those described above may have a relatively large cross-sectional area or a relatively short mid-span region. Examples of such specimens include round and square bars up to and exceeding 20 millimeters in diameter or per side. When such large specimens are mechanically tested, not only must the electrical connections to these specimens be sufficiently large and strong to carry the requisite heating current but the mechanical connections, through the jaw assemblies, to both ends of the specimen must be adequate to control and maintain and accurately transmit the forces required for compressive and/or tensile testing to the specimen. Furthermore, when specimens are tested at uniform temperatures, it is a common well-known standard ASTM (American Society for Testing and Materials) practice in the art to slightly reduce the cross-sectional area of the mid-span region of the specimen in order to induce fracturing to occur therein. In specimens that have a circular cross-sectional area, this reduction is readily accomplished by reducing the diameter of the specimen along a relatively large radius starting with a zero percentage reduction at an inward end of each jaw contact region and extending inward with gradually increasing reductions until a 1% reduction occurs at the center of the mid-span region of the specimen.

Furthermore, each jaw assembly can include appropriate conductors that are shaped to provide the necessary self-inductive and self-resistive heating in order to establish a desired longitudinal thermal gradient end-to-end along the entire specimen. In this case, the testing specimen can have a substantially uniform cross-section. In this regard, FIG. 4 shows a detailed plan view of a tension/compression test apparatus which forms a portion of the dynamic thermal-mechanical testing system and that incorporates jaw assemblies fabricated in accordance with my inventive teachings.

As shown, specimen 600 is held between two jaw assemblies 401 and 401', both of which are identical, mounted in load frame 416. Jaw assembly 401' is stationary; while jaw assembly 401 is moved laterally by piston rod 419 of hydraulic cylinder 420 so as to impart a desired tensile/compressive force to the specimen. The cylinder is connected through hydraulic ports 421 to a suitable servo controlled hydraulic system (well known and not shown) to accurately control the relative movement between the jaw assemblies and hence the tensile and compressive forces imparted to specimen 600. Stationary jaw assembly 401' is connected to the load frame through load cell 417. This load cell accommodates relatively little movement, typically on the order of 0.1 mm, for a full load. Both jaw assemblies are connected through flexible leads 414 and 414' to high current AC power supply 130 in order to route heating current from the supply serially through both the jaw assemblies and the specimen. These leads are secured by fasteners (typically bolts) 431 and 431' to both jaw assemblies and appropriate output terminals of the power supply. In operation and during one-half cycle of applied AC power, heating current (I) flows in the directions shown by arrows 443, 440 and 442; while, during the next successive half-cycle, the heating current reverses its direction. To prevent current from flowing into hydraulic cylinder 420, insulating disk 418 is situated between and abuts against both moveable jaw assembly and one end of piston rod 419.

Figure 6:
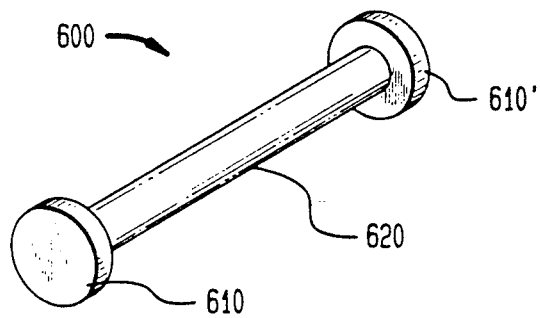
FIG. 6 shows an illustrative "button-end" cylindrical test specimen, having a circular cross-section, that can be used in conjunction with my inventive jaw assemblies shown in either FIGS. 4 or 5.

Specimen 600, also shown in FIG. 6, has two buttons 610 and 610' of substantially equal cross-sectional area machined on opposing ends thereof. Between these buttons, the specimen has a substantially uniform transverse cross-sectional area. Alternatively, each opposing end of specimen 600 may be threaded with a nut being appropriately used to restrain the specimen within each jaw assembly. Jaw assemblies 401 and 401' respectively contain wedge grip pairs 402 and 402' which are fabricated from a high strength insulating material, including any one of a variety of well known ceramic or composite materials, and are retained within jaw bodies 408 and 408'. Both jaw bodies are fabricated from any one of several well known materials that will withstand the high forces used in mechanically deforming the specimen at the maximum test temperature. These jaw assemblies may be water-cooled, if desired. Jaw bodies 408 and 408' have a wedge pocket with taper sections 409 and 409', respectively, that each has a taper matching on a complementary basis the outer taper on each of the wedge grips. This taper is approximately 10 degrees as measured to the axis of the specimen. Each of the wedge grips has a machined groove along its inner contour that accurately fits the outer peripheral contour of the specimen. The wedge grip pairs are situated on specimen, as shown, such that the grip contact area on the specimen is located inward of each button. Wedge grip pairs 402 and 402' (as well as wedge grips 509 and 509, shown in FIG. 5) may also be pneumatically operated in order to provide a uniform gripping force along a relatively wide specimen fabricated from sheet stock. As depicted in FIG. 4, conductors 403 and 403', each being preferably a strip shaped to resemble a "U" or an elongated oval (as shown), abut against each end-face of the specimen. Blocks 404 and 404', made of a suitably high strength insulating material—typically any one of many well known ceramic materials, are placed within the conductors both to prevent their deformation during compressive testing and to force current flow completely through these conductors. The materials used for these blocks is selected, based upon the expected stress level therein and the maximum test temperature, from any one of several well known materials such that during compression testing, the thickness of these blocks and the overall width of each conductor can be minimized. Alternatively, the so-called "best available" materials can be used for all tests, though such materials may be prohibitively costly. Once the appropriate material has been selected, then the compression strain on the combined thickness of conductors 403 and 403' (two wall thicknesses in each as shown) and the corresponding block will substantially remain at its lowest point.

Conductors 403 and 403' form the heating sections and hence provide both self-inductive and self-resistive heating in the manner described in detail above. These conductors are appropriately sized and shaped to impart a requisite amount of heat into both end-faces of specimen 600 that offsets the heat losses that occur from the specimen into both jaw assemblies thereby assuring that substantially no longitudinal thermal gradients appear along the entire specimen during heating. Based upon the amount of self-inductive and self-resistive heat desired, conductors 403 and 403' may each have one or two U-shaped heating sections. If each of these conductors is formed to have two such sections 406 and 407, or 406' and 407' (as shown), then each such section should have approximately the same shape and cross-sectional area so that it will carry approximately one-half of the total current flowing through the specimen. If specimen 600 is low carbon steel and approximately 10 millimeters in diameter thereby providing a cross-sectional area of approximately 78.5 square millimeters and conductors 403 and 403' are each fabricated from 2 millimeter thick sheet stock that has substantially the same electrical and thermal resistivity as the specimen, then the width of the conductor used to form each heating sections 406, 407, 406' and 407' will be approximately 19.6 millimeters. Alternatively, if each sheet stock based conductor were to have only one heating section, then the cross-section of this section should approximately match that of the low carbon steel specimen—the thickness of the conductor would either be twice as thick as that used to fabricate sections 406, 407, 406' and 407' or lessened but with the latter requiring an increase in the width of the conductor.

The thickness of blocks 404 and 404' determines the spacing between the vertical legs of each heating section and hence determines the degree of magnetic coupling therebetween and self-inductive heat that will be generated therein. Each of these conductors may be shaped from a flat piece of material that has been formed to have two opposing symmetric 180 degree bends that produce two corresponding heating sections. The interface between each of conductors 403 and 403' and a corresponding end-face of specimen 600 should preferably be only a mechanical butt joint without any other type of connection. Not only will each of the conductors heat an end of the specimen but these conductors will also thermally advantageously isolate that end from the mechanical/jacking components, which will soon be described, as well as the other high current conductors.

As noted above, the material used to form each of conductors 403 and 403' can be any one of many well known conductive ferrous or non-ferrous materials, as discussed above, which can undergo self-resistive heating and in which a suitable amount of eddy currents can be induced, with the specific material being selected based on its high temperature strength and the mechanical compressive force that will be involved in testing the specimen, the type of specimen being tested, the anticipated current level, the maximum test temperature and the expected time at that temperature. If testing is to occur up to approximately 1000° C., then conductors 403 and 403' can each be fabricated from type 304 austenitic stainless steel. Other materials, such as INCONEL type 718 alloy or RENE' type 95 nickel-based alloys may also be used for these conductors (INCO- NEL and RENE' are trademarks of International Nickel Company and General Electric Company, respectively) particularly since their high temperature properties surpass those of austenitic stainless steels. In those situations where specimen 600 may exhibit a tendency to stick to conductors 403 and 403', a thin sheet (not specifically shown), typically between 0.1 -0.25 millimeter, of an appropriate material, such as carbon or tantalum, may be placed between each end-face of the specimen and each abutting conductor. Such a sheet, which prevents welding, would likely reduce any such sticking which would otherwise occur between the specimen end-face and the conductor surface as the specimen is being crushed during compression testing and arising from high temperature at the button, high force, possible diffusion bonding thereat and/or welding. Such a sheet can also be similarly and advantageously used with the jaw assemblies shown in FIGS. 5 or 8, both of which are discussed in detail below.

Conductors 403 and 403' abut against conductive washers 410 and 410' which, in turn, abut against high current bands 412 and 412', respectively. These washers provide a uniform contact area between the conductors and the bands. The combination of conductors 403 and 403' and blocks 404 and 404' are respectively compressed through washers 410 and 410' by corresponding screw jacks 411 and 411' so as to assure a tight abutting mechanical and serial electrical connection among the bands, washers and conductors. The screw jacks expand the overall width of bands 412 and 412'. Each band may be fabricated using a number of laminations of copper strip in order to provide flexibility and handle high currents without generating much heat therefrom. To prevent current from flowing through screw jacks 411 and 411', these jacks are insulated from bands 412 and 412' by corresponding insulating disks 413 and 413'.

Inasmuch as high current bands 412 and 412' are typically formed of copper and are in contact, through washers 410 and 410', with conductors 403 and 403' which produce self-inductive and self-resistive heat, these bands should be water-cooled to limit their temperature. This may be readily accomplished by water cooling jack nuts 424 and 424' which respectively contact bands 412 and 412'. Alternatively, a separate water-cooled "chill" block having good thermal conductivity may be inserted between each jacks and an interior surface of the corresponding band. In either case, the longevity of the life of the bands will be adversely shortened if these bands are not properly cooled during high current testing.

Figure 5:
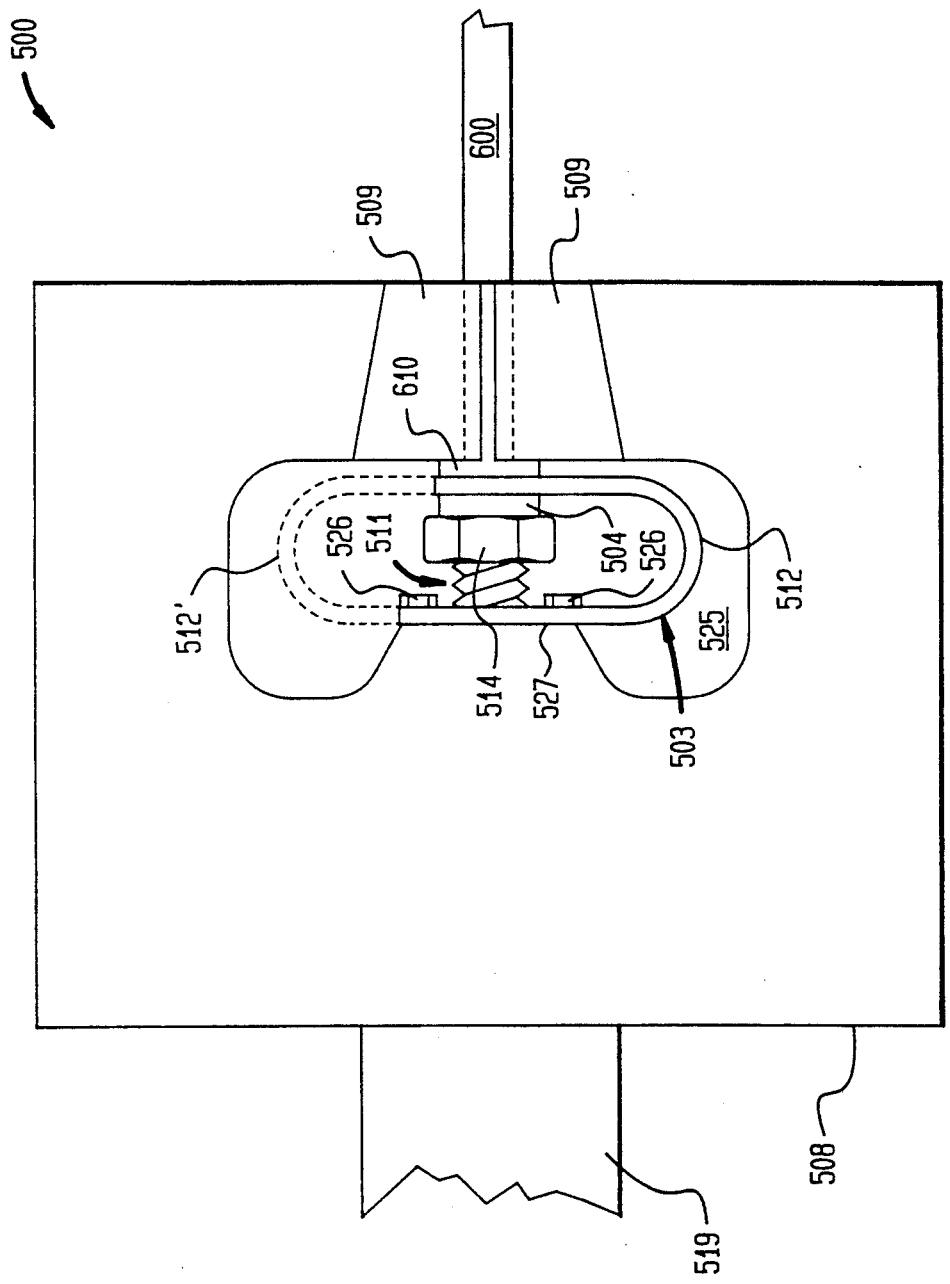
FIG. 5 shows an alternate and simplified embodiment of my inventive jaw assembly that can be used in the tension/compression test apparatus shown in FIG. 4.

FIG. 5 shows an alternate and simplified embodiment of my inventive jaw assembly that can be used in the tension/compression apparatus shown in FIG. 4. Inasmuch as an identical jaw assembly is secured to the opposing side of specimen 600 partially shown in FIG. 5, then to simplify the drawing, only jaw assembly 500 is depicted in this figure and will be specifically described below.

Body 508 of jaw assembly 500 can be fabricated from austenitic stainless steel or high strength aluminum, neither of which is ferromagnetic. Certainly, other materials can be used for body 508, but any other such material should not be ferromagnetic in order to maximize the electrical performance of the jaw assembly, specifically the amount of self-inductive heat that is generated in conductive band 503 and imparted to the specimen end. Pocket 525 is machined into jaw body 508 and runs completely transversely through the jaw body, i.e. in a direction perpendicular to the plane of the figure. Similar to jaw assemblies 401 and 401' shown in FIG. 4 and described in detail above, pocket 525 shown in FIG. 5 includes a wedge pocket with 10 degree taper sections oriented with respect to a longitudinal axis of the specimen. A pair of wedge grips 509 and 509', each having an external taper that matches that of the wedge pocket, abuts against opposing sides of this pocket. Here too, wedge grips 509 and 509' mutually grasp the specimen such that the grip contact area on the specimen is located inward of button 610. Each wedge grip has an internal contour that accurately matches the outer peripheral contour of specimen 600: round for specimens having a circular cross-section and flat for sheet specimens having a rectangular or square crosssection.

Wedge grips 509 and 509' are fabricated from a high strength insulating material. As noted above, this material may be a ceramic or composite material that provides good thermal and good electrical insulation. These wedge grips, as well as those shown in FIG. 4 and described above, may also be made of a combination of metallic and insulating materials provided the specimen is well insulated from the jaw body. Conductive band 503, which provides both good thermal and electrical conduction, contains either one or two heating sections 512 and 512' and functions in the same manner to generate self-inductive and self-resistive heat as do conductors 403 and 403' shown in FIG. 4 and discussed in detail above. As depicted in FIG. 5, one end of band 503 abuts against and electrically contacts end button 610 of specimen 600, while the other end of this band is rigidly secured, by fasteners 526, in tight abutting electrical contact to jaw body 508 and specifically to surface 527 thereof which protrudes into pocket 525. If band 503 is fabricated of material that has essentially the same electrical and thermal resistivity as specimen 600, then the band, if it is formed to contain only one heating section (e.g. section 512), should have approximately the same cross-sectional area as the midspan region of the specimen in order to prevent essentially any longitudinal thermal gradients from appearing along the entire specimen during heating. Of course, as noted above, the cross-section of band 503 and the material used to fabricate it can be appropriately chosen in order to provide a desired non-zero longitudinal thermal gradient along the specimen. Also, the overall width of the band as well as the length of the legs existing therein can be modified to provide a desired degree of inductive coupling therebetween and self-inductive heating therefrom. Since the band will typically heat to a temperature in excess of the "Curie temperature" for ferritic materials, then, as described above, the band can be either ferrous or non-ferrous. In this regard, austenitic stainless steels and nickel, both of which are non-ferrous, are two suitable materials from which band 503 can be fabricated. If specimen 600 is low carbon steel, then its resistance will be less than stainless steel or nickel which, in turn, will permit band 503 to possess an increased cross-sectional area than that of the specimen.

Inasmuch as band 503 will generate considerable heat, the heat which propagates to surface 527 of jaw body 508 must be conducted away from this surface. Accordingly, jaw body 508 should be water-cooled preferably through use of water passages machined into the jaw body.

Specimen 600 is tightly secured in place through screw jack 511. This jack is threaded into jaw body 508 and is adjusted so hex jack nut 514 forces insulating washer 504 tightly against an end-face of button 610 of the specimen. Inasmuch as the screw jack and hex nut 514 are both metallic, washer 504, which provides good thermal and electrical insulation, prevents both current and heat from flowing through the screw jack. Use of the washer advantageously permits compressive force to be transmitted through the screw jack to the specimen while forcing electrical current to flow through conductive band 503. To extend the life of the jack threads (not specifically shown) in the jaw body, these threads can contain stainless steel helicoil inserts mounted in an aluminum body. Screw jack 511 may be replaced by a suitable pneumatic or hydraulic system. For example, a piston and cylinder may be located in jaw body 508. An end of a piston rod would then protrude through a hole in band 503 and, when properly extended, exert suitable mechanical force on washer 504.

Shaft 519 provides mechanical and electrical connections from the remainder of the dynamic thermal-mechanical testing system to jaw body 508. Cooling water can also be channeled bi-directionally through the shaft to and from the jaw assembly.

As noted above, specimens of differing sizes and shapes and materials can be used with my inventive jaw assemblies. In this regard, FIG. 6 shows an illustrative "button-end" cylindrical test specimen 600, having a circular cross-section, that can be used in conjunction with my inventive jaw assemblies shown in either FIGS. 4 or 5.

Here, specimen 600 is formed by appropriately machining a cylindrically shaped piece of material to produce mid-span region 620 spanned at opposing ends thereof by buttons 610 and 610'. This specimen can be used for both compressive and tensile testing. Each button has a larger cross-sectional area than at its mid-span region. However, to permit a constant heating rate to occur longitudinally throughout the button and the mid-span region, the size of the button (i.e. its diameter and thickness) is chosen such that, if the button were viewed as a washer situated on the end of the specimen with a hole equal in diameter to the specimen diameter, the total inner circumferential surface area of the button would equal the cross-sectional area of the specimen itself (equal at both of its ends and at its mid-span region). As such, if no electrical or thermal current were to flow between the end of the specimen itself and the button, the thermal density that would radially occur from the inner perimeter of the button would equal that which would flow through a cross-section of the specimen itself. If the buttons were to be eliminated and abutting contact established between the ends of the specimen alone and conductors 403 and 403', then the resulting thermal and electrical contact areas to the specimen would likely be too small for use with relatively large sized specimens and particularly for the thermal and electrical currents associated therewith. While experimental tests have indicated that the size of the button is not critical, nevertheless, the button should not either be too small so as to cause excessively high current densities which might cause welding to occur or too large so as to impart excessive thermal mass to the ends of the specimen and conduct excess heat therefrom. In the event a button were to be too large, then that button would disadvantageously heat at a slower rate than the mid-span region and undesired longitudinal thermal gradients would appear in the specimen. A portion of the mechanical force produced by the testing system is transmitted through friction occurring from the wedge grips to the contact surface of the specimen. This friction is enhanced by jacking the specimen into place, as described above. Accordingly, each button only needs to support the force imparted by each jaw assembly that exceeds the frictional holding force in the wedge grip. Alternatively, the buttons can be replaced by nuts threaded onto the ends of the specimen, though this arrangement is likely to provide thermal and electrical conduction that is inferior to that resulting from use of buttons.

Figure 7:
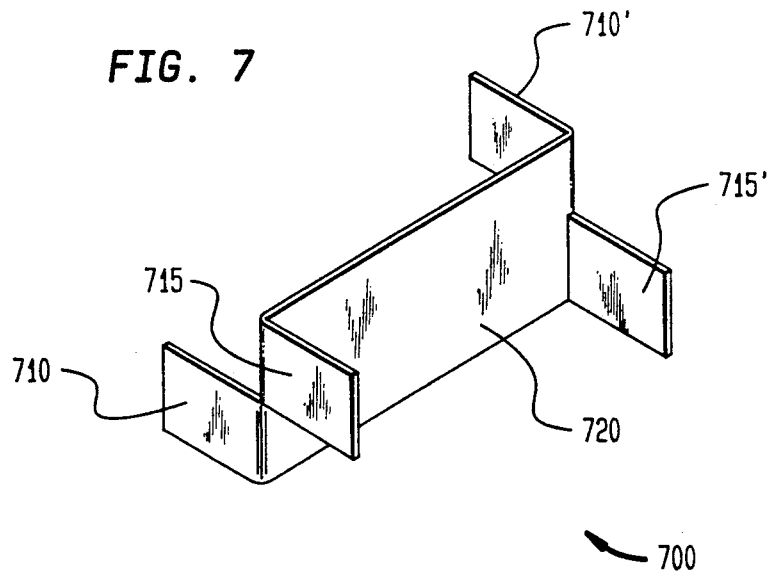
FIG. 7 shows an illustrative "bent-end" sheet metal test specimen, having a rectangular cross-section, that can also be used in conjunction with my inventive jaw assemblies shown in either FIGS. 4 or 5.

FIG. 7 shows an illustrative "bent-end" sheet metal test specimen 700, having a rectangular cross-section, that can also be used in conjunction with my inventive jaw assemblies shown in either FIGS. 4 or 5. This specimen, formed of sheet metal and having a rectangular cross-section, is often used for tensile testing. As shown, specimen 700 is formed, typically by bending, to contain two bent tabs 710, 715 and 710', 715', respectively, at each end thereof. Each pair of these tabs located at an end of the specimen abuttingly contacts the "self-inductive/self-resistive" conductor(s) in a corresponding jaw assembly and establishes good thermal and electrical contact between that jaw assembly and the specimen. While many other specimen shapes are possible, FIGS. 6 and 7 illustrate the two shapes that are expected to be principally used in most dynamic thermal-mechanical material tests.

If, through use of my invention, a uniform temperature is established throughout a specimen that has a mid-span region with a uniform cross-sectional area, then during testing, that specimen can fracture at any point along the its length. Well-known standardized procedures, as described above, are generally used to initially form such specimens with slightly reduced mid-span cross-sectional areas such that during room temperature testing fractures can be induced to occur along the mid-span region. The amount of any such reduction is governed by specifications for the test specimen that is to be used in a particular test. Inasmuch as my invention advantageously permits a uniform elevated temperature to be established either along the entire length of a specimen or merely along its mid-span region, a similar reduction in mid-span cross-sectional area can also be used with specimens that are to undergo heating in order to control the location of the fracture region therein.

Figure 8:
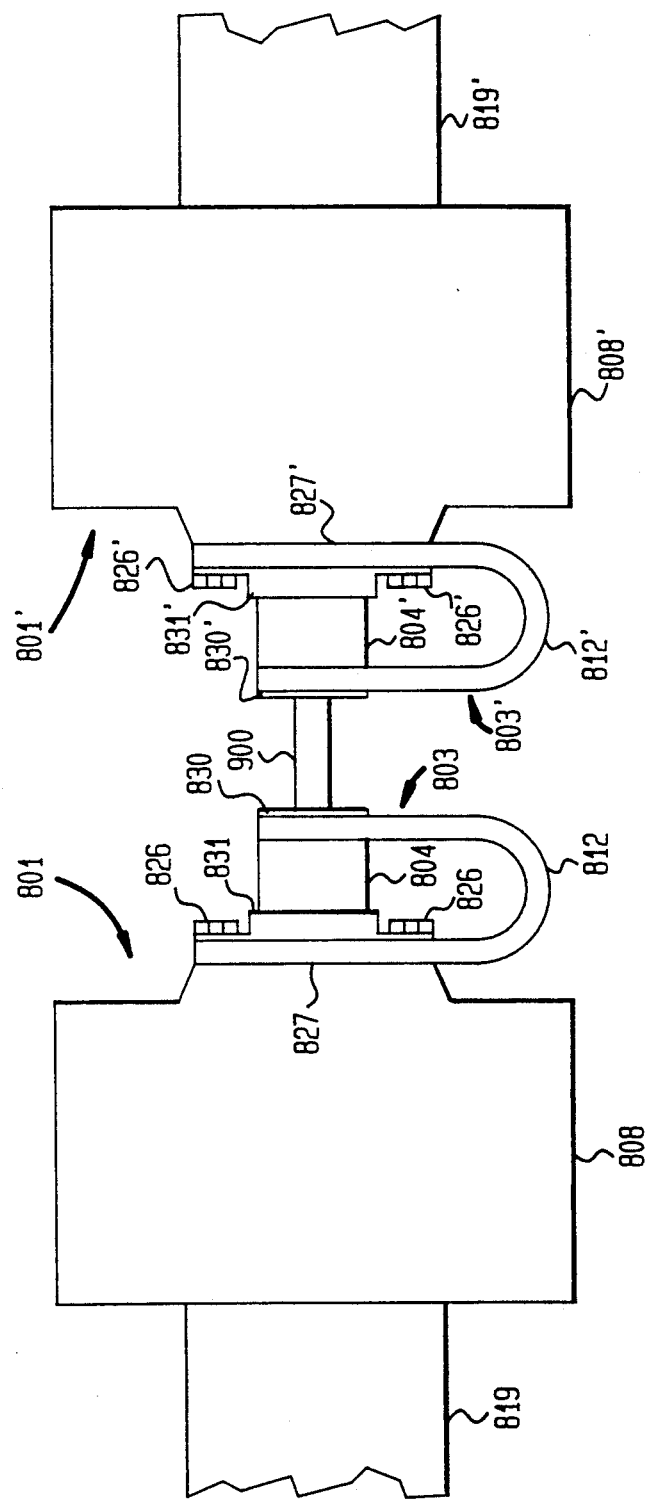
FIG. 8 shows a further embodiment of my inventive jaw assemblies that can be used to compressively test "slug" type specimens.

FIG. 8 shows a further embodiment of my inventive jaw assemblies that can be used for compressively testing "slug" type specimen 900, particularly for hot flow stress testing. A slug specimen is a cylindrical specimen of completely uniform cross-sectional area in which the length of the specimen is usually less than three times the specimen diameter; with the latter typically being on the order of 10 or 12 millimeters. A slug specimen has no buttons on its ends. Here, flat jaws rather than wedge grips are used to hold specimen 900, with the specimen being retained between identical jaw assemblies 801 and 801' merely by a compressive force exerted on the specimen by both jaw assemblies. During specimen heating, this compressive force is generally just sufficient to reduce the electrical and thermal resistances at the interfaces between each end of the specimen and a jaw assembly thereby assuring good electrical and thermal flow therebetween. Conductive bands 803 and 803' conduct electric current from jaw bodies 808 and 808' to opposite ends of specimen 900. Both of these conductors are formed to possess an approximately 180 degree bend and provide heating sections 812 and 812' which function in the specific manner described in detail above. One end of conductive bands 803 and 803' is attached at interfaces 827 and 827' to jaw bodies 808 and 808' by fasteners 826 and 826', respectively. These fasteners also secure clamps 831 and 831'. Insulating blocks 804 and 804' (specifically insulating anvils), which are similar to blocks 404 and 404' (see FIG. 4), support the outer ends of conductive bands 803 and 803' in place and are also secured to jaw bodies 808 and 808' by respective fasteners 826 and 826'. These bands may be over bent to provide a desired amount of positional friction that holds the outer ends of these bands in place or may be secured by appropriate well-known fasteners (not shown) to the outer surfaces of both insulating blocks. After heating has occurred and during subsequent compression testing, slug specimen 900 increases in cross-sectional area as it decreases in length. As a result of this deformation, sliding occurs at the ends of the specimen. This sliding can disadvantageously cause the specimen ends to stick or weld to conductive bands 803 and/or 803'. To provide appropriate lubrication between the conductive bands and the specimen ends and thereby avoid any such sticking and/or welding, thin sheet 830, 830' of a suitable material (such as tantalum or carbon, as discussed above) can be situated between each end of specimen 900 and a neighboring conductive band 803, 803', respectively. Connecting shafts 819 and 819' transmit mechanical compressive forces to jaw bodies 808 and 808' from the remainder of the dynamic thermal-mechanical testing system, carry electrical heating current therefrom to the jaw bodies and also bi-directionally channel cooling water to and from the jaw bodies.

Clearly, while my invention has been described in terms of providing heating sections in the specimen itself and near both ends thereof or in conductor(s) formed within jaw assemblies and which abut against both of these ends, any number of such heating sections can be associated with each such end, regardless of whether an equal number of such sections is associated with each end. More sections can be used at one end than the other. In fact, one end can have no such sections associated therewith, while the other end has one or more such sections associated therewith. The number and/or location(s) of all of these sections on the specimen itself or the number of such sections located within each jaw assembly will be governed by the desired thermal gradient, if any, that is to be longitudinally established throughout the specimen.

Although various embodiments which incorporate the teachings of my present invention have been shown and described in detail herein, those skilled in the art can readily devise many other varied embodiments that still incorporate these teachings.

I claim:

1. A testing specimen for undergoing controlled heating in a materials testing system having two opposing jaw assemblies for retaining the specimen at opposing ends thereof, said heating to occur by virtue of an alternating current that is to be supplied by said system and will flow through said specimen, wherein the specimen is formed of a pre-defined conductive material capable of being self-resistively heated and having eddy current flow induced therein, said specimen comprising:

a mid-span region centrally located between the opposing ends of the specimen; and a heating section formed in the specimen at a location intermediate said mid-span region and at least one of said ends, wherein said heating section has a pre-defined shape and size such that said section will undergo self-induction in response to flow of the alternating current through said specimen and generate both self-inductive and self-resistive heat therein which, in conjunction with self-resistive heat generated in the mid-span region of the specimen by said current, will establish a pre-defined longitudinal thermal gradient along the mid-span region during the controlled heating of the specimen.

2. The specimen in claim 1 wherein said specimen comprises two heating sections, wherein each one of said sections is situated intermediate said mid-span region and a different corresponding one of said ends.

3. The specimen in claim 2 wherein said alternating current occurs at power line frequencies.

4. The specimen in claim 3 wherein said material is a pre-selected conductive ferrous or non-ferrous material.

5. The specimen in claim 4 wherein each of said sections comprises a portion of said specimen fabricated into a substantially oval shape with respect to a longitudinal axis of the specimen.

6. The specimen in claim 4 wherein each of said sections comprises a portion of said specimen fabricated into a substantially U shape with respect to a longitudinal axis of the specimen.

7. The specimen in claim 4 wherein each of said sections comprises a portion of said specimen fabricated into a substantially triangular shape with respect to a longitudinal axis of the specimen.

8. The specimen in claim 4 wherein each of said sections is formed by bending said specimen into said pre-defined shape.

9. A materials testing system having a jaw assembly for retaining an end of a test specimen and for supplying alternating electrical current thereto so as to cause controlled heating to occur in the specimen by virtue of the current flowing therethrough, said jaw assembly comprising:

a heating conductor one end of which is in abutting electrical contact with an end of said specimen for conducting the current between said conductor and said specimen, said conductor being formed of a pre-defined conductive material capable of generating self-resistive heat and having eddy current flow induced therein, wherein said conductor comprises:

at least one heating section formed therein, said section having a pre-defined shape and size such that the section will undergo self-induction in response to flow of the alternating current serially passing through said conductor and said specimen and will generate self-inductive and self-resistive heat in the conductor such that a portion of the heat will be conductively transmitted into the end of the specimen where, in conjunction with self-resistive heat generated in the specimen by the current, will establish a pre-defined longitudinal thermal gradient through the specimen during the controlled heating thereof.

10. The testing system in claim 9 wherein asid alternating current occurs at power line frequencies.

11. The testing system in claim 10 wherein said material is a pre-selected conductive ferrous or non-ferrous material.

12. The testing system of claim 11 wherein said conductor has a substantially oval shape.

13. The testing system of claim 11 wherein said conductor has a substantially U shape.

14. The testing system in claim 11 wherein said conductor has a substantially triangular shape.

15. The testing system in claim 11 wherein said system comprises two substantially identical jaw assemblies for retaining said specimen therebetween, each of said assemblies having a corresponding jaw body, wherein both jaw bodies are connected to corresponding terminals of an alternating current power supply for providing said alternating current to said jaw assemblies and to said specimen.

16. The testing system in claim 15 wherein each one of said jaw assemblies comprises a pocket extending transversely through said corresponding jaw body and said heating conductor is situated within said pocket, said pocket further comprises a conductive band situated therein and in abutting electrical contact with an inner surface of said pocket and in electrical communication with said conductor for conducting said electrical current between said corresponding jaw body and said conductor so as to establish a serial current path between one end of said specimen and said one jaw assembly.

17. The testing system in claim 14 wherein said pocket comprises a pair of opposing tapered surfaces and said corresponding jaw body further comprises a pair of insulating wedge grips each of said grips having a tapered outer surface complimentary to either one of said tapered surfaces in said pocket for mounting in an abutting relationship thereto, wherein each of said wedge grips has an inner contour which substantially matches an outer peripheral contour of specimen.

18. The testing system of claim 17 wherein said corresponding jaw assembly further comprises means separately situated between opposing inner surfaces of said conductive band and the heating conductor for respectively preventing said conductive band and said conductor from deforming during compression testing of said specimen and for forcing the alternating current to flow through the band and the conductor.

19. The testing system in claim 15 wherein each one of said jaw assemblies comprises a pocket extending transversely through said corresponding jaw body and said heating conductor is situated within said pocket, wherein an end of said conductor is in abutting electrical contact with an inner surface of said pocket so as to establish a serial current path through said conductor and between one end of said specimen and said one jaw assembly.

20. The testing system in claim 19 wherein said pocket comprises a pair of opposing tapered surfaces and said corresponding jaw body further comprises a pair of insulating wedge grips each of said grips having a tapered outer surface complimentary to either one of said tapered surfaces in said pocket for mounting in an abutting relationship thereto, wherein each of said wedge grips has an inner contour which substantially matches an outer peripheral contour of specimen.

21. The testing system in claim 20 wherein said corresponding jaw assembly further comprises means situated between opposing inner surfaces of said conductor for preventing said conductor from deforming during compression testing of said specimen and for forcing the alternating current to flow through the conductor.

22. The testing system in claim 15 wherein said corresponding jaw body further comprises passages formed therein to permit a pre-defined fluid to flow therethrough in order to cool the jaw body during testing.

23. In a materials testing system having two opposing jaw assemblies for retaining a testing specimen at opposing ends thereof and for passing alternating current therethrough to controllably heat the specimen, said specimen being formed of a pre-defined conductive material capable of being self-resistively heated and having eddy current flow induced therein and comprising a mid-span region centrally located between the opposing ends of the specimen and a heating section formed in the specimen at a location intermediate said mid-span region and at least one of said ends, wherein said heating section has a pre-defined shape and size such that said section will undergo self-induction in response to flow of the alternating current through said specimen and generate both self-inductive and self-resistive heat therein, a method comprising the step of:
controllably passing alternating current through said jaw assemblies and said specimen so as to generate self-inductive and self-resistive heat therein which, in conjunction with self-resistive heat generated in mid-span of the specimen by said current, produces a pre-defined longitudinal thermal gradient along the mid-span region during the controlled heating of the specimen.

24. The method in claim 23 further comprising the step of forming two heating sections in said specimen, wherein each one of said sections is situated intermediate said mid-span region and a different corresponding one of said ends.

25. The method in claim 24 wherein said alternating current occurs at power line frequencies.

26. The method in claim 25 wherein said material is a pre-selected conductive ferrous or non-ferrous material.

27. The method in claim 26 wherein said forming step comprises the step of fabricating a portion of said specimen into a substantially oval shape with respect to a longitudinal axis of the specimen so as to form each of said sections.

28. The method in claim 26 wherein said forming step comprises the step of fabricating a portion of said specimen into a substantially U shape with respect to a longitudinal axis of the specimen so as to form each of said sections.

29. The method in claim 26 wherein said forming step comprises the step of fabricating a portion of said specimen into a substantially triangular shape with respect to a longitudinal axis of the specimen so as to form each of said sections.

30. In a materials testing system having two substantially identical opposing jaw assemblies for retaining a testing specimen at opposing ends thereof and for passing alternating current therethrough to controllably heat the specimen, each of said jaw assemblies having a heating conductor one end of which is in abutting electrical contact with one end of said specimen for conducting the current between said conductor and said specimen, asid conductor being formed of a pre-defined conductive material capable of generating self-resistive heat and having eddy current flow induced therein, wherein asid conductor comprises at least one heating section formed therein, said section having a pre-defined shape and size such that the section will undergo self-induction in response to flow of the alternating current serially passing through said conductor and said specimen and generate both self-inductive and self-resistive heat in said conductor, a method comprising the step of:

controllably passing alternating current through said conductor and said specimen so as to generate both self-inductive and self-resistive heat in said conductor such that a portion of said heat will be conductively transmitted from said conductor into said one end of the specimen so as to produce, in conjunction with self-resistive heat generated in the specimen by said current, a pre-defined longitudinal thermal gradient through the specimen during the controlled heating thereof.

31. The method in claim 30 wherein said alternating current occurs at power line frequencies.

32. The method in claim 31 wherein said material is a pre-selected conductive ferrous or non-ferrous material.

33. The method in claim 32 said conductor has a substantially uniform rectangular or square cross-sectional area and said method further comprises the step of forming said conductor to have a substantially oval shape.

34. The method in claim 32 said conductor has a substantially uniform rectangular or square cross-sectional area and said method further comprises the step of forming said conductor to have a substantially U shape.

35. The method in claim 32 said conductor has a substantially uniform rectangular or square cross-sectional area and said method further comprises the step of forming said conductor to have a substantially triangular shape.

* * * * *